United States Patent [19]
Long et al.

[11] 3,980,705
[45] Sept. 14, 1976

[54] PURIFICATION OF ROBENIDINE HYDROCHLORIDE

[75] Inventors: Don Wesley Long, Trenton; Robert Arthur Ralston, Lebanon, both of N.J.

[73] Assignee: American Cyanamid Company, Stamford, Conn.

[22] Filed: May 19, 1975

[21] Appl. No.: 578,574

[52] U.S. Cl. .................................................. 260/564 F
[51] Int. Cl.² ........................................... C07C 133/10
[58] Field of Search ................................... 260/564 F

[56] References Cited
UNITED STATES PATENTS 3,769,432  10/1973  Tomcufcik ........................ 424/326

*Primary Examiner*—Gerald A. Schwartz
*Attorney, Agent, or Firm*—Denis A. Polyn

[57] ABSTRACT

A superior grade of 1,3-bis(4-chlorobenzylideneamino)-guanidine hydrochloride is obtained by dispersing crude material in a suitable solvent, slowly adding to the dispersion an amount of base at least equivalent to the number of moles of 1,2,3-tris(4-chlorobenzylideneamino)guanidine hydrochloride present in said crude 1,3-bis(4-chlorobenzylideneamino)guanidine hydrochloride, separating the purified 1,3-bis(4-chlorobenzylideneamino)guandidine hydrochloride therefrom, and washing and drying the same.

5 Claims, No Drawings

PURIFICATION OF ROBENIDINE HYDROCHLORIDE

BACKGROUND OF THE INVENTION

This invention relates to the purification of 1,3-bis-(4-chlorobenzylideneamino)guanidine hydrochloride (robenidine hydrochloride). More particularly, this invention relates to the purification of 1,3-bis(4-chlorobenzylideneamino)guanidine hydrochloride by selectively converting a contaminant salt to the corresponding free base which is soluble in the reaction medium. Still more particularly, this invention relates to the purification of 1,3-bis(4-chlorobenzylideneamino)guanidine hydrochloride by selectively converting any 1,2,3,tris(4-chlorobenzylideneamino)-guanidine hydrochloride therein to the free base and recovering the 1,3-bis(4-chlorobenzylideneamino)-guanidine hydrochloride in a higher state of purity.

Robenidine, usually administered as the hydrochloride, is a coccidiostat for the treatment of chickens. U.S. Pat. No. 3,769,432 to Tomcufcik, the full disclosure of which is hereby incorporated by reference, discloses the preparation and use of robenidine hydrochloride. The preparation is carried out by the reaction of N,N'-diaminoguanidine hydrochloride (I) and 4-chlorobenzaldehyde (II) as shown below:

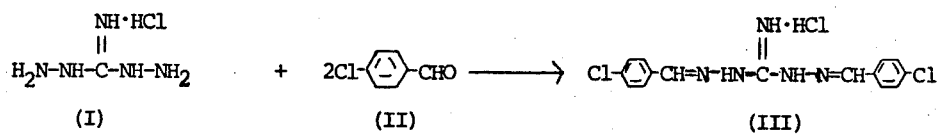

This process for the production of robenidine hydrochloride (III) results in a product which is pharmacologically acceptable. However, depending on the amount of N,N',N''-triaminoguanidine hydrochloride impurity present in the starting N,N'-diaminoguanidine hydrochloride, the product may have to be repeatedly recrystallized in order to lower the concentration of 1,2,3-tris(4-chlorobenzylideneamino)guanidine hydrochloride (IV)

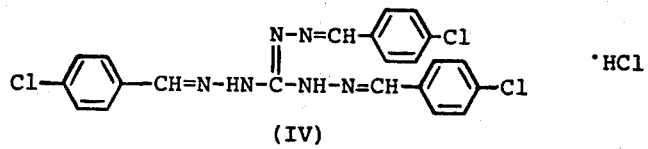

contaminant to an acceptable level. This process of Tomcufcik usually results in a product having a melting point of 289°–290°C., with decompostion, and contains from about 1% to 3% by weight of 1,2,3-tris(4-chlorobenzylideneamino)guanidine hydrochloride after recrystallization from aqueous alcoholic solution. However, the product can contain as much as 7% of 1,2,3-tris(4-chlorobenzylideneamino)guanidine hydrochloride if the starting material (I) is very impure.

BRIEF SUMMARY OF THE INVENTION

It has now been found that a product having superior quality is consistently obtained in acceptable yields by forming a slurry of crude 1,3-bis(4-chlorobenzylideneamino)guanidine hydrochloride in a suitable solvent, or mixture of suitable solvents, preferably in acetone. Depending on the amount of unreated 4-chlorobenzaldehyde or hydrolysis product still present in the material, the apparent pH of the slurry may require adjustment to about 4.6 by adding base thereto. If the concentration of unreacted 4-chlorobenzaldehyde or hydrolysis product is very low, then no adjustment of pH is required. To the stirred slurry at ambient temperature (15°–30°C.) is added at least one molar equivalent of a suitable base per mole of 1,2,3-tris(4-chlorobenzylideneamino)quanidine hydrochloride contaminant present in the crude material. Stirring is then continued for a short period at ambient temperature after the addition of the base is completed. Preferably, the temperature is raised to about 35°–55°C. after the addition of the base is completed, and the reaction mixture is then cooled to ambient conditions and filtered to recover the purified 1,3-bis(4-chlorobenzylideneamino)guanidine hydrochloride which is washed successively with water and a suitable solvent, preferably acetone, and dried. The process of this invention results in a product which contains less than 3%, usually less than 1% of 1,2,3-tris(4-chlorobenzylideneamino)guanidine hydrochloride as a contaminant.

DETAILED DESCRIPTION OF THE INVENTION

In accordance with the present invention, crude robenidine hydrochloride is dispersed in a suitable solvent such as acetone, methanol, isopropanol, aqueous isopropanol containing at least 50 percent by volume of isopropanol, benzene, toluene, chloroform, and the like, at a temperature of about 15°–30°C. to form an easily-stirred slurry. Generally, from about 2.9 to about 3.3 parts by weight of solvent is used per part by weight of crude robenidine hydrochloride on a dry basis. The preferred solvents are acetone, isopropanol, and aqueous isopropanol.

Sufficient suitable base is first added to the slurry to adjust the apparent pH to about 4.6. The adjustment of the apparent pH to about 4.6 is important because the presence of contaminants such as 4-chlorobenzoic acid or 4-chlorobenzaldehyde can consume base and reduce the effectiveness of the base in neutralizing 1,2,3-tris(4-chlorobenzylideneamino)guanidine hydrochloride. If the crude material contains only 1,2,3-tris(4-chlorobenzylideneamino)guanidine hydrochloride as the contaminant, then adjustment of the pH is not necessary. As used herein, the term "apparent pH" is defined as the pH value obtained by carrying out the measurement in a solvent which is not entirely water.

Also as used herein, the term "suitable base" is defined as a base such as sodium hydroxide, potassium hydroxide, ammonium hydroxide, ammonia, triethylamine, triethanolamine, sodium bicarbonate, sodium carbonate, potassium bicarbonate, sodium methoxide, and 1,2,3-bis(4-chlorobenzylideneamino)guanidine.

The slurry is stirred at ambient temperature, preferably about 25°C., and then suitable base is gradually added thereto over a period from about 1/6 hour to about 2 hours while maintaining the temperature at about 25°C. to about 30°C. The amount of said suitable base added to the slurry at this point is at least sufficient to convert all of the 1,2,3-tris(4-chlorobenzylideneamino)guanidine hydrochloride present to the free base. Generally, from 1 to 4 molecular equivalents of base, preferably from about 1.5 to about 2.0 molecular equivalents, are added per mole of 1,2,3-tris(4-chlorobenzylideneamino)guanidine hydrochloride present in the crude material. Since the 1,2,3-tris(4-chlorobenzylideneamino)guanidine hydrochloride is a by-product of the reaction of 4-chlorobenzaldehyde and N,N',N''-triaminoguanidine hydrochloride, the number of moles of base to be added to the slurry can be determined by determining the concentration of N,N',N''-triaminoguanidine hydrochloride present in the starting N,N'-diaminoguanidine hydrochloride.

After the addition of the base is completed the slurry is stirred at ambient temperature, preferably about 25°C., for an additional one to two hours and then filtered. Preferably, after the addition of the base is completed the slurry is heated to about 35°-55°C., over a period of about ½ to about 1 hour, and then cooled to about 20°-35°C. The slurry is filtered at 15°-45°C., preferably at 25°C., to separate the robenidine hydrochloride. The crystals are then washed successively with water and a suitable solvent, such as acetone or isopropanol, at ambient temperature and dried at a temperature of from about 20°C, to about 120°C. Centrifugation, or other methods of solid separation, may be used instead of filtration where solid and liquid separation is required.

The invention is illustrated by the following examples in which parts are by weight unless otherwise clearly indicated.

EXAMPLE 1

An isopropanol-wet sample of 60.5 grams of crude 1,3-bis(4-chlorobenzylideneamino)guanidine hydrochloride which contains 3.06% by weight (0.0036 mole) of 1,2,3-tris(4-chlrorobenzylideneamino)guanidine hydrochloride is charged to a flask containing 242 ml. of acetone at room temperature to form a slurry. The apparent pH of the slurry is then increased from 1.8 to 4.6 by adding 2 drops of 50% sodium hydroxide thereto. To the slurry is added 0.72 g. (0.009 mole) of 50% sodium hydroxide over a period of 10 minutes while maintaining the temperature below 25°C. The slurry is stirred and heated to about 50°C., and cooled to about 25°C., over a period of 2 hours. The solid is filtered off, washed successively with 100 ml. of water and 100 ml. of acetone, and dried to obtain 53.98 grams (89.2% recovery) of white crystals of 1,3-bis(4-chlorobenzylidenamino)guanidine hydrochloride which contains 0.95% by weight of 1,2,3-tris(4-chlorobenzylideneamino)guanidine hydrochloride.

EXAMPLE 2

The procedure of Example 1 is followed, using the same crude 1,3-bis(4-chlorobenzylideneamino)guanidine hydrochloride, except that the apparent pH is not adjusted to 4.6 before adding the 0.72 g. of 50% sodium hydroxide. There is obtained 54.8 grams (90.6% recovery) of light yellow crystals of 1,3-bis(4-chlorobenzylideneamino)guanidine hydrochloride which contains 3.27% by weight of 1,2,3-tris(4-chlorobenzylideneamino)guanidine hydrochloride.

This example demonstrates the importance of prior adjustment of the apparent pH to about 4.6.

EXAMPLE 3

To 121 ml. of acetone is added 32.5 g. of crude 1,3-bis(4-chlorobenzylideneamino)guanidine hydrochloride which contains 13.1 weight percent of 1,2,3-tris(4-chlorobenzylideneamino)guanidine hydrochloride as an impurity. The slurry is heated to 45°-50°C. over about 15 minutes while stirring, maintained at 45°-50°C. for 30 minutes, and the cooled to 25°C. The solid is filtered off, washed with 50 ml. of water followed by 50 ml. of acetone, and dried at 80°C. for 2 hours. There is obtained 31.47 grams (98.6% recovery) of product which on analysis is found to contain 13.2 weight percent of 1,2,3-tris-(4-chlorobenzylideneamino)guanidine hydrochloride.

This example shows that 1,2,3-tris(4-chlorobenzylideneamino)guanidine hydrochloride cannot be removed from crude 1,3-bis(4-chlorobenzylideneamino)guanidine hydrochloride by simply slurrying the material in acetone at 45°-50°C.

EXAMPLE 4

The procedure and starting material of Example 3 are used except that 1.35 g. of 50% sodium hydroxide (0.0169 mole) is added over a period of 5 minutes while stirring at 25°C. prior to heating to 45°-50°C. Filtration, washing, and drying gives 24.5 g. (75.4% recovery) of very light yellow product which on analysis is found to contain 0.8 weight percent of 1,2,3-tris(4-chlorobenylideneamino)guanidine hydrochloride.

This example shows that the addition of two moles of sodium hydroxide to the slurry per mole of 1,2,3-tris(4-chlorobenzylideneamino)guanidine hydrochloride present in the crude significantly reduces the percentage of the same material in the final product.

EXAMPLE 5

A 15.0 g. sample of crude 1,3-bis(4-chlorobenzylideneamino)guanidine hydrochloride which contains more than 1% (0.15 g., 0.0003 mole) of 1,2,3-tris(4-chlorobenzylideneamino)guanidine hydrochloride as an impurity is dispersed in a mixture of 200 ml. of isopropanol and 10 ml. of water at room temperature. To the stirred dispersion is added a solution of 0.24 g. of 50% sodium hydroxide (0.003 mole) is 10 ml. of water at room temperature over a period of 5 minutes. The dispersion is stirred for an additional hour at room temperature, filtered, washed with 50 ml. of isopropanol and dried. Assay of the air-dried product by thin-layer chromatography shows no 1,2,3-tris(4-chlorobenzylideneamino)guanidine hydrochloride present.

EXAMPLE 6

A 10.0 g. sample of crude 1,3-bis(4-chlorobenzylideneamino)guanidine hydrochloride, which contains about 2.5% by weight (0.25 g.; 0.0005 mole) of 1,2,2-tris(4-chlorobenzylideneamino)guanidine hydrochloride as an impurity, is charged to a mixture of 70 ml. of chloroform and 10 ml. of water to form a dispersion. To the dispersion is added 0.08 g. (0.001 mole) of 50% sodium hydroxide while stirring at room temperature. The mixuture is then heated to 50°C. while stirring over a period of about 10 minutes, cooled over about 30 minutes to about 35°C., filtered, washed with 15 ml. of chloroform and air dried. Analysis of the product by thin layer chromatography shows that no 1,2,3-tris(4chlorobenzylideneamino)guanidine hydrochloride is present.

EXAMPLES 7–10

In Examples 7–10 a mixture of 10.0 grams of 1,3-bis(4-chlorobenzylideneamino)guanidine hydrochloride and 1.372 grams of 1,2,3-tris(4-chlorobenzylideneamino)guanidine hydrochloride (which contains 12.0% of the latter compound based on the weight of the mixture) is charged to a flask equipped with a stirrer, thermometer, and reflux-condenser and 84 ml. of acetone are added thereto form a slurry. To the slurry is added 0.00540 mole of a suitable base over a period of about 5–10 minutes at 25°C. The reaction mixture is then heated to 50°C., slowly cooled to 25°C. over a period of about 30 minutes, and filtered. The filter cake is washed with 50 ml. of water, twice with 50 ml. portions of acetone, and air dried. The final product is then weighed and analyzed for percent 1,2,3-tris(4-chlorobenzylideneamino)guanidine hydrochloride. The results obtained are reported in Table I.

TABLE I

| Example | Base* | Weight (grams) | Recovery (%) | "tris-hydrochloride" (%) |
|---|---|---|---|---|
| 7 | (a) | 9.0 | 90.0 | 0.45 |
| 8 | (b) | 8.4 | 84.0 | 0.54 |
| 9 | (c) | 8.5 | 85.0 | 0.15 |
| 10 | (d) | 10.6 | 88.3 | 0.31 |

*(a) 0.545 g. (0.0054 mole) of triethylamine plus 0.54 g. of water
(b) 0.308 g. of 28% aqueous ammonia (0.0054 mole) plus 0.8 g. of water
(c) 0.54 g. of anhydrous potassium carbonate (0.0054 mole) in 2 ml. of water
(d) 1.80 g. (0.0054 mole) of 1,3-bis(4-chlorobenzylidencamino)guanidine in 10 ml. of acetone.

These results illustrate the operation of the process of the invention with various bases using two moles of base per mole of 1,2,3-tris(4-chlorobenzylideneamino)guanidine hydrochloride present initially.

EXAMPLE 11

To 20 ml. of acetone at about 25°C. is added 2.67 grams of crude 1,3-bis(4-chlorobenzylideneamino)-guanidine hydrochloride which contains 13.1% by weight of 1,2,3-tris(4-chlorobenzylideneamino)guanidine hydrochloride (0.3498 g., 0.00069 mole) to form a slurry. To the slurry is added 0.110 g. of 50% sodium hydroxide (0.0014 mole) over a period of about 5 minutes. The resulting mixture is then stirred at 25°C. for 3 hours and then filtered to separate the insoluble product. The product is then washed with 20 ml. of water, followed by 20 ml. of acetone, and dried. There is obtained 2.0 grams (74.9% recovery) of product which contains 0.44% of 1,2,3-tris-(4-chlorobenzylideneamino)guanidine hydrochloride.

This example shows that purification can be effected without the heating step after the addition of base is carried out.

EXAMPLE 12

The assay procedure for determining the amount of 1,2,3-tris(4-chlorobenzylideneamino)guanidine hydrochloride ("tris" impurity) in robenidine hydrochloride is carried out as follows.

I. Reagents

1. Chloroform: reagent grade
2. Methanol: reagent grade
3. Triethylamine: reagent grade
4. Hydrochloric Acid: concentrated, reagent grade
5. 0.5M Triethylamine in Chloroform: weight 50.6 g. of triethylamine and dilute to 1 liter with chloroform.

II. Special Apparatus

1. Woelum Aluminum Oxide — Activity Grade 1: Waters Associates Inc., Farmington, Massachusetts.
2. Chromatographic Tube: 15 mm. i.d. × 150 mm. long equipped with a Teflon stopcock and glass fritted disc. Supplied by Fischer Porter Company.
3. Actinic Glass Volumetric Flask: 25, 100, 200, and 250 ml. capacity.

III. Column Preparation

1. Prepare a slurry of about 20 g. alumina (neutral) and 30 ml. of chloroform in a 125 ml. beaker.
2. Fill the 15 × 150 mm. column to a height of about 8 cm. with the slurry.
3. Lower the solvent of the slurry to the packing and add 10 ml. of methanol. Again lower the solvent level to the bed.
4. Wash the alumina column with 40 ml. of chloroform. When the solvent has reacted the top of the alumina, the column is ready for use.

IV. Assay Procedure

Accurately weigh 0.20–0.22 g., weighed to the nearest 0.1 mg., of the sample directly into a 10 ml. volumetric flask. Let W = the sample weight in grams. Add enough 0.5M triethylamine in chloroform to completely dissolve the sample. Dilute to volume with the same solvent and mix well. Introduce 2 ml. (volumetric pipet) of the sample solution onto the top of the alumina column. Control the flow from the pipet directing it against the side of the column, so that disturbance of the bed is minimum. Place a 25 ml. volumetric flask containing a 1 inch funnel under the column tip. Adjust the flow rate to approximately 40 drops per minute. When the solution just reaches the top of the alumina bed, gently add 2 ml. of chloroform while washing down the inside of the column. After lowering the solvent to the packing, repeat the 2 ml. chloroform process one more time. When this portion has been lowered to the bed surface, elute the column with an additional 16 ml. of chloroform. Lower the chloroform to the packing and stop the flow. Dilute the column eluent in the 25 ml. volumetric flask to volume with chloroform and mix well (Solution A). Pipet 2.0 ml. (volumetric pipet) of Solution A into a 100 ml. volumetric flask containing 50 ml. methanol. Swirl to facilitate solution. Add 3 drops (medicine dropper) of concentrated hydrochloric acid to the flask, dilute to volume with methanol and mix well. (Solution B). Measure the ultraviolet absorbance of Solution B at 318 nm using methanol as the reference.

Calculations

% Tris Impurity = $(A_B \times 4.044/w)$ where $A_B$ = the absorbance of Solution B at 318 nm, $W$ = the sample weight in grams and
the absorptivity (1 g./cm.) of the tris purity at 318 mn is 154.54.

We claim:
1. The process of purifying crude 1,3-bis(4-chlorobenzylideneamino)guanidine hydrochloride contaminated with 1,2,3-tris(4-chlorobenzylideneamino)guanidine hydrochloride which comprises the steps of:
   a. slurrying the crude 1,3-bis(4-chlorobenzylideneamino)guanidine hydrochloride in a suitable stirred solvent;
   b. adjusting the apparent pH of said slurry to about 4.6;
   c. adding to said slurry from 1 to 4 molar equivalents of a suitable base selected from the group consisting of sodium hydroxide, potassium hydroxide, sodium bicarbonate, sodium carbonate, triethylamine, trimethylamine, and 1,3-bis(4-chlorobenzylideneamino)guanidine per mole of 1,2,3-tris(4-chlorobenzylideneamino)guanidine hydrochloride present in said crude 1,3-bis-(4-chlorobenzylideneamino)guanidine hydrochloride over a period of from 10 minutes to about a few hours;
   d. stirring said slurry at from about 20°C. to about 30°C. for a period of from about 10 minutes to about a few hours after the addition of the base is completed; and
   e. recoverying the insoluble 1,3-bis(4-chlorobenzylideneamino)guanidine hydrochloride therefrom.

2. The process according to claim 1 wherein after the addition of the base is completed the slurry is heated to a temperature of from about 35°C. to about 55°C., then cooled to ambient temperature, and the insoluble 1,3-bis(4-chlorobenzylideneamino)guanidine hydrochloride recovered therefrom.

3. The process according to claim 2 wherein 2 molar equivalents of a suitable base are added per mole of 1,2,3-tris(4-chlorobenzylideneamino)guanidine hydrochloride and wherein said slurry is heated to a temperature of from about 45°C. to about 50°C.

4. The process according to claim 1 wherein said suitable solvent is selected from the group consisting of acetone, isopropanol, chloroform, diethyl ether, aqueous isopropanol containing at least 50% by volume of isopropanol, and a mixture of chloroform and water.

5. The process according to claim 1 wherein said recovered 1,3-bis(4-chlorobenzylideneamino)guanidine hydrochloride is subsequently washed with water at about 20°C. to about 25°C., washed with said suitable solvent at about 20°C. to about 25°C., and dried at a temperature of from about 25°C. to about 120°C.

* * * * *